(12) United States Patent
Ju

(10) Patent No.: US 11,884,908 B2
(45) Date of Patent: Jan. 30, 2024

(54) 3D CELL AUTOMATED INCUBATOR

(71) Applicant: DANAGREEN CO., LTD., Seoul (KR)

(72) Inventor: Seung Yon Ju, Seoul (KR)

(73) Assignee: Danagreen Co., Ltd., Seoul (KR)

( * ) Notice: Subject to any disclaimer, the term of this patent is extended or adjusted under 35 U.S.C. 154(b) by 533 days.

(21) Appl. No.: 17/057,294

(22) PCT Filed: May 13, 2019

(86) PCT No.: PCT/KR2019/005685
§ 371 (c)(1),
(2) Date: Jan. 20, 2021

(87) PCT Pub. No.: WO2019/225893
PCT Pub. Date: Nov. 28, 2019

(65) Prior Publication Data
US 2021/0214666 A1    Jul. 15, 2021

(30) Foreign Application Priority Data

May 21, 2018   (KR) ........................ 10-2018-0057885

(51) Int. Cl.
*C12M 1/12*   (2006.01)
*C12M 3/00*   (2006.01)
(Continued)

(52) U.S. Cl.
CPC ............ *C12M 25/14* (2013.01); *C12M 21/08* (2013.01); *C12M 23/22* (2013.01); *C12M 23/34* (2013.01);
(Continued)

(58) Field of Classification Search
None
See application file for complete search history.

(56) References Cited

U.S. PATENT DOCUMENTS

| | | | | |
|---|---|---|---|---|
| 4,952,510 A | * | 8/1990 | Gabridge | ............... C12M 23/08 435/288.2 |
| 5,766,949 A | * | 6/1998 | Liau | ....................... C12M 25/06 435/395 |

(Continued)

FOREIGN PATENT DOCUMENTS

| JP | H10-191961 A | 7/1998 |
|---|---|---|
| JP | 2004-089137 A | 3/2004 |

(Continued)

OTHER PUBLICATIONS

International Search Report and Written Opinion dated Aug. 9, 2019 in International Application No. PCT/KR2019/005685, in 9 pages. (English translation of ISR.).

(Continued)

*Primary Examiner* — Holly Kipouros
(74) *Attorney, Agent, or Firm* — Knobbe, Martens, Olson & Bear, LLP

(57) ABSTRACT

This application relates to an automated three-dimensional (3D) cell culture system. The system includes a first body including a cell culture space in which a scaffold, on which cells are cultured, is provided and the cells are cultured thereon, and a medium storage space which is partitioned from the cell culture space by a first partition wall, in which a medium is provided and stored, and which surrounds the cell culture space, wherein the first partition wall has a drain hole to communicate the medium storage space with the cell culture space. The system also includes a communication pipe provided at the first partition wall to drain the medium of the cell culture space to the outside by a siphon action. The system further includes a second body including a medium recovery space located under the first body and recovering and externally draining the medium drained through the communication pipe.

11 Claims, 5 Drawing Sheets

(51) Int. Cl.
*C12M 1/00* (2006.01)
*C12M 1/34* (2006.01)

(52) U.S. Cl.
CPC ............ *C12M 23/38* (2013.01); *C12M 29/00* (2013.01); *C12M 37/04* (2013.01); *C12M 41/44* (2013.01)

(56) References Cited

U.S. PATENT DOCUMENTS

| | | |
|---|---|---|
| 2014/0287451 A1 | 9/2014 | McFetridge |
| 2015/0218503 A1 | 8/2015 | Kiyama et al. |
| 2017/0226462 A1* | 8/2017 | Wu ................. C12M 29/10 |
| 2019/0264156 A1* | 8/2019 | Hagihara ............ C12M 23/06 |

FOREIGN PATENT DOCUMENTS

| | | |
|---|---|---|
| JP | 2004-242619 A | 9/2004 |
| JP | 2008-154579 A | 7/2008 |
| JP | 2012-005411 A | 1/2012 |
| WO | WO 2016/072460 A1 | 5/2016 |
| WO | 2017/062629 A1 | 4/2017 |

OTHER PUBLICATIONS

Search Report of the corresponding European Application No. 19807628.3, dated Jul. 15, 2021.
1st Office Action of the corresponding Japanese Application No. 2021-516342, dated Feb. 1, 2022.
2nd Office Action of the corresponding Japanese Application No. 2021-516342, dated Sep. 27, 2022.

* cited by examiner

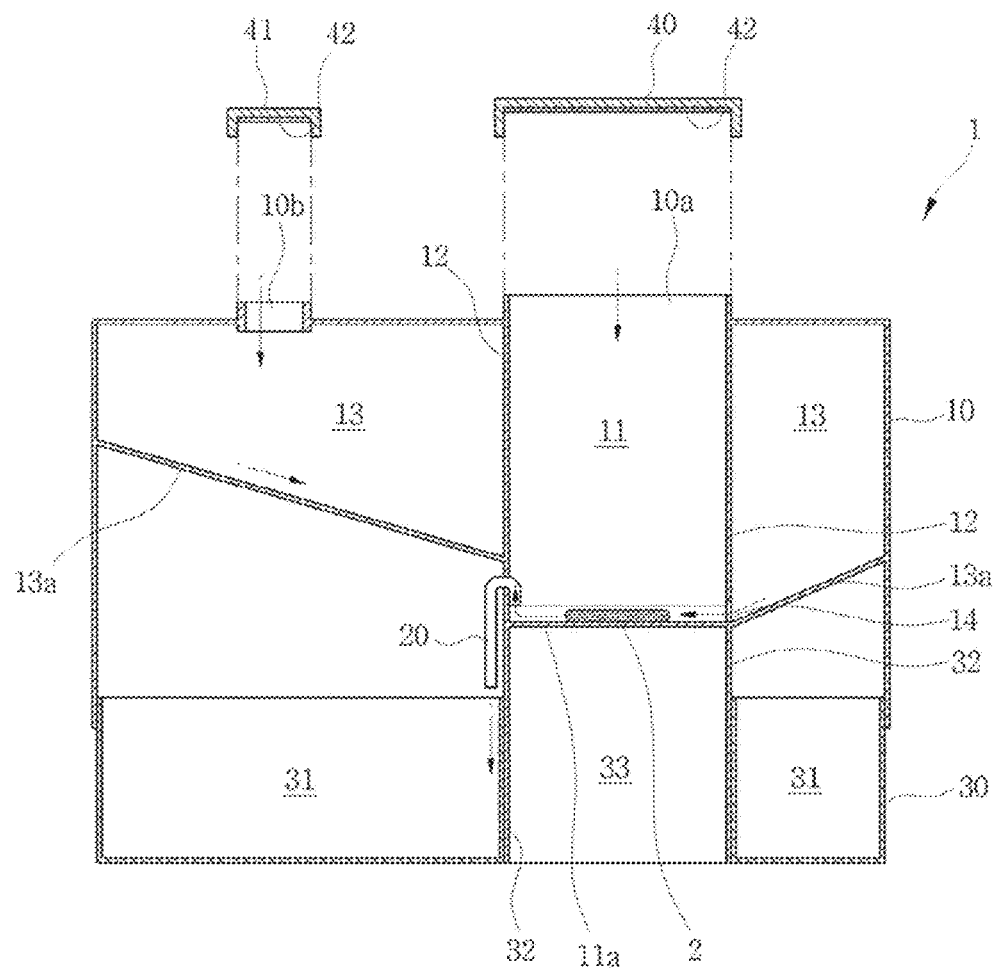

3D CELL AUTOMATED INCUBATOR

The present application is a U.S. national phase application under 35 U.S.C. § 371 of International Application No. PCT/KR2019/005685, filed on May 13, 2019, which claims the benefit of Korean Patent Application No. 10-2018-0057885 filed on May 21, 2018, in the Korean Intellectual Property Office, the entire disclosure of each of which is incorporated herein by reference.

TECHNICAL FIELD

The present disclosure relates to an automated three-dimensional (3D) cell culture system. More specifically, the present disclosure relates to an automated 3D culture system in which cells are cultured by automatically providing a medium to cells that can be cultured to be artificial organs such as the skin, the liver, or the heart.

BACKGROUND ART

In one of methods of culturing cells, cells are seeded on a cell culture dish, and an appropriate amount of medium is provided to culture the cells.

However, for long-term culture and continuous observation of cells, there is a need to exchange the medium several times. In addition, while the medium is exchanged several times, it is highly likely for culture cells to be out of the cell culture dish and contaminated. Accordingly, the improvement of the cell culture system is needed.

Meanwhile, automated cell culture devices that have been publicly disclosed or have already been widely used undergo, for example, frequent failures due to internal moisture, which is one of the problems of the devices, and may require higher maintenance costs.

Therefore, up until now, the automated cell culture using devices is not available now. That is, since cells need to be cultured for a long period of time to make cells into artificial organs such as the skin, the liver, or the heart, there is a demand for a device capable of culturing cells stably and efficiently.

DESCRIPTION OF EMBODIMENTS

Technical Problem

The objective of the present disclosure is to simultaneously address a number of problems that could not be solved in the prior art, so that a medium is automatically supplied to cells and the cells are continuously cultured and observed for a long time.

The objective of the present disclosure is to provide an automated 3D culture system that enables easy long-term culture by automatically supplying a medium to cells that can be cultured into artificial organs such as the skin, the liver, or the heart.

Technical Problem

One or more embodiments include an automated three-dimensional (3D) culture system including: a first body including a cell culture space in which a scaffold, on which cells are cultured, is provided and the cells are cultured thereon, and a medium storage space which is partitioned from the cell culture space by a first partition wall, in which a medium is provided and stored, and which surrounds the cell culture space, wherein the first partition wall has a drain hole to communicate the medium storage space with the cell culture space;

a communication pipe provided at the first partition wall to drain the medium of the cell culture space to the outside by a siphon action; and a second body consisting of a transparent material and including a medium recovery space located under the first body and recovering and externally draining the medium drained through the communication pipe, and a cell observation space partitioned from the medium recovery space by a second partition wall to observe cells from the outside.

In the automated 3D culture system according to an embodiment of the present disclosure, the first body and the second body may be integrally formed, or separated so as to be disassembled and assembled, and a drain port for draining the medium is formed at a lower portion of the second body integrally formed with the first body.

In the automated 3D culture system according to an embodiment of the present disclosure, a lower end of the medium storage space may be formed to have a horizontal cross-section which is formed in a diagonal direction or constitutes a V-shaped valley with reference to a drain hole.

In the automated 3D culture system according to an embodiment of the present disclosure, each of the first body and the second body has a polygonal or circular horizontal cross-section, and the first partition wall and the second partition wall are located at the central portions of the first body and the second body, respectively, and each have a polygonal or circular horizontal cross-section.

In the automated 3D culture system according to an embodiment of the present disclosure, the drain hole and the communication pipe may be arranged opposite to each other, or arranged in such a direction that the communication pipe crosses the drain hole.

In the automated 3D culture system according to an embodiment of the present disclosure, the automated 3D culture system may include a first lid for opening and closing the cell culture space and a second lid for opening and closing the medium storage space.

In the automated 3D culture system according to an embodiment of the present disclosure, the first lid and the second lid may each be provided with a sealing pad thereinside to seal the cell culture space or the medium storage space.

In the automated 3D culture system according to an embodiment of the present disclosure, the process of providing the medium into the medium storage space and the process of providing the scaffold and the cells into the cell culture space may be performed in a clean bench.

In the automated 3D culture system according to an embodiment of the present disclosure, the medium of the cell culture space may be drained to the communication pipe by a siphon action, when the medium of the cell culture space is filled as high as the maximum level of the communication pipe.

In the automated 3D culture system according to an embodiment of the present disclosure, the first body and the second body may each include a transparent material.

In the automated 3D culture system according to an embodiment of the present disclosure, a lowermost portion of the end of the communication pipe may be formed at a position higher than the drain hole of the first partition wall.

These solutions will become more apparent from the detailed description for carrying out the following disclosure based on the accompanying drawings.

The terms or expressions used in the present specification and claims should not be interpreted in such a manner as conventionally understood and defined in dictionaries. Based on the principle in which the inventors should appropriately define the concept of terms in order to explain the present disclosure in the best manner, the terms and the expressions must be interpreted as a meaning and concept consistent with the technical idea of present disclosure.

Advantageous Effects Of Disclosure

According to an embodiment of the present disclosure, a medium is repetitively provided via an automated supply in a one-way low method by using a medium storage space partitioned from a cell culture space by a first partition wall and thus separately formed therefrom, a communication pipe, and a medium recovery space, enabling the automated culture of cells for a long period of time.

In addition, through a cell observation space separated from the medium recovery space by being partitioned through the second partition wall, cells can be continuously observed so that compatibility with external devices for photographing the growth of specific parts of the cells or motion patterns thereof may be obtained. Therefore, the present disclosure is effective in terms of being able to easily culture cells into, for example, artificial organs such as the skin, the liver, or the heart.

BRIEF DESCRIPTION OF DRAWINGS

FIG. 5 shows a cross-sectional view of an automated 3D culture system according to an embodiment of the present disclosure to describe a cell culture process.

MODE OF DISCLOSURE

Figure 1:
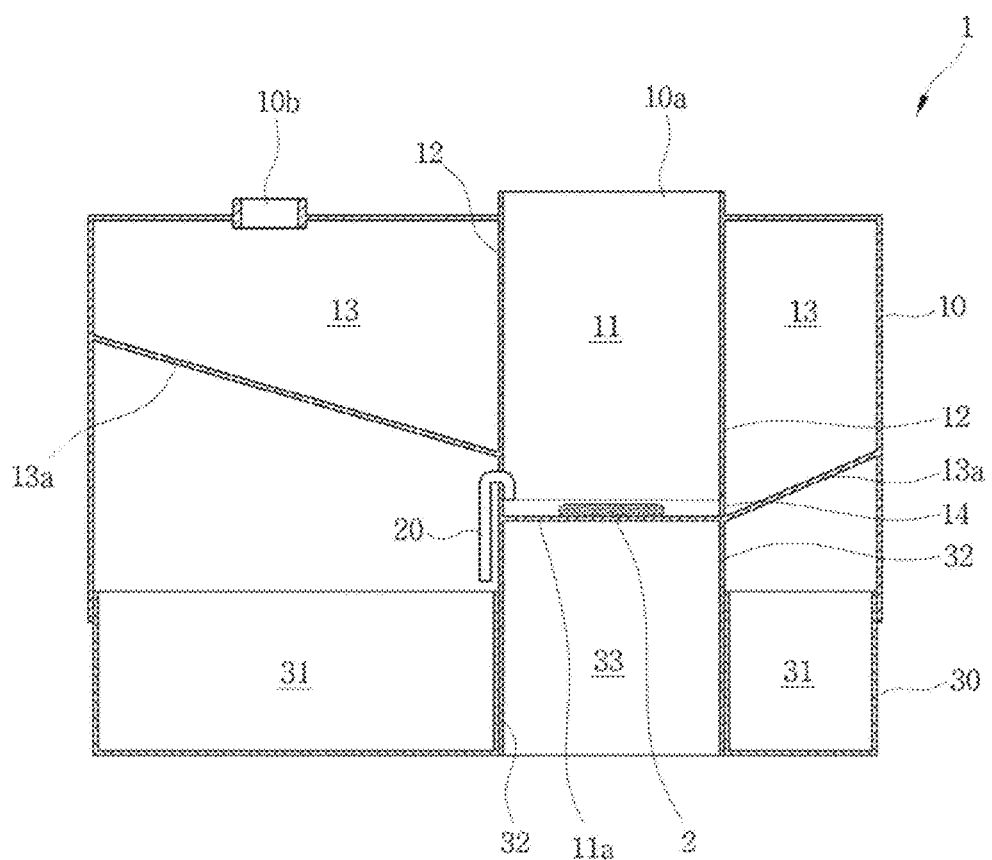
FIG. 1 shows a cross-sectional view of the interior of an automated three-dimensional (3D) culture system according to an embodiment of the present disclosure.

The specific viewpoints and specific technical features of the present disclosure will become apparent from the following specific description and embodiments related to the accompanying drawings. In the present specification, in relation to adding reference numerals to elements of each drawing, the same elements have the same reference numerals although they are indicated on different drawings. In addition, in describing embodiments of the present disclosure, when it is determined that a detailed description of a related known configuration or function may make the subject matter of the present disclosure unclear, a detailed description thereof will be omitted.

In addition, in describing the components of the present disclosure, terms such as first, second, A, B, (a), and (b) may be used. These terms are only used to distinguish one component from another component, and the nature, sequence, or order of the corresponding component is not limited by the terms. When a component is described as being "connected", "coupled" or "linked" to another component, the component may be directly connected or linked to the other component, or other components may be "connected", "coupled" or "linked" to therebetween.

Hereinafter, an embodiment of the present disclosure will be described in detail with reference to the accompanying drawings.

FIG. 1 shows a cross-sectional view of the interior of an automated three-dimensional (3D) culture system 1 according to an embodiment of the present disclosure, in which a cell culture space 11 and a medium storage space 13, which are partitioned by a first partition wall 12 and formed to be separated from each other, are provided inside a first body 10, a medium recovery space 31 and a cell observation space 33, which are partitioned by a second partition wall 32 and formed to be separated from each other, are provided inside a second body 30, and a communication pipe 20 is provided on the first partition wall 12.

Figure 2:
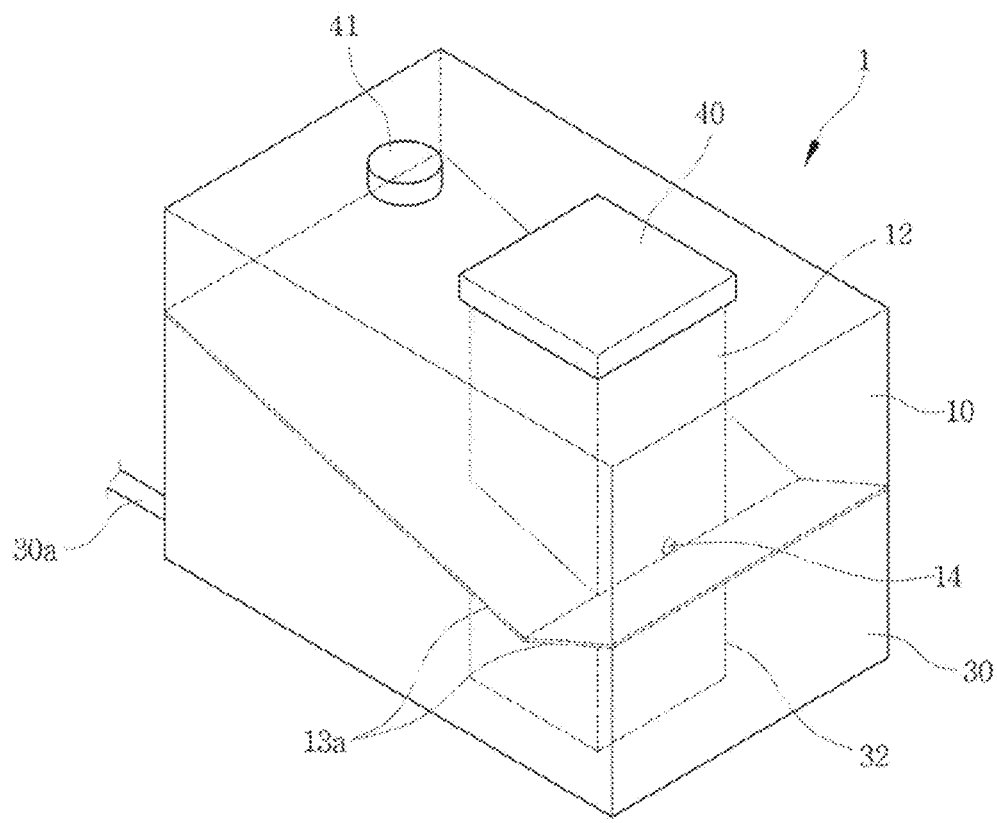
FIG. 2 shows a perspective view of an automated 3D culture system according to an embodiment of the present disclosure.

FIG. 2 shows a perspective view of the automated 3D culture system 1 according to an embodiment of the present disclosure, in which the first body 10 and the second body 30 are integrally formed, a lower end 13a of the medium storage space 13 forms a V-shaped valley with respect to a drain hole 14 inside the first body 10, and a drain port 30a is formed at the second body 30.

Figure 3:
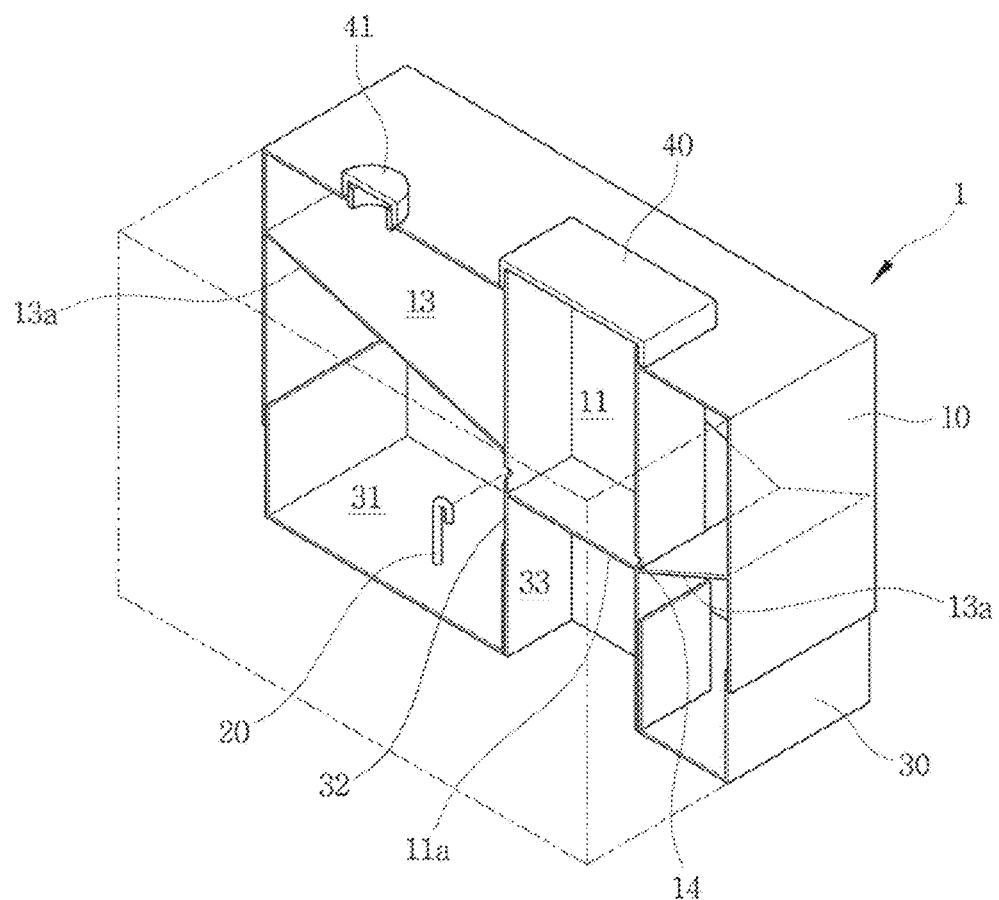
FIG. 3 shows a perspective view of a cross-section of a 3D culture system according to an embodiment of the present disclosure.

FIG. 3 shows a perspective view of a cross-section of the automated 3D culture system 1 according to an embodiment of the present disclosure, in which the cell culture space 11 and the medium storage space 13, which are partitioned by the first partition wall 12 and formed separately from each other, are provided inside the first body 10, a first lid 40 and a second lid 41 for opening and closing the cell culture space 11 and the medium storage space 13 are provided above the first body 10, the medium recovery space 31 and the cell observation space 33, which are partitioned by the second partition wall 32 and formed to be separated from each other, are provided inside the second body 30, and the communication pipe 20 is provided on the first partition wall 12.

Figure 4:
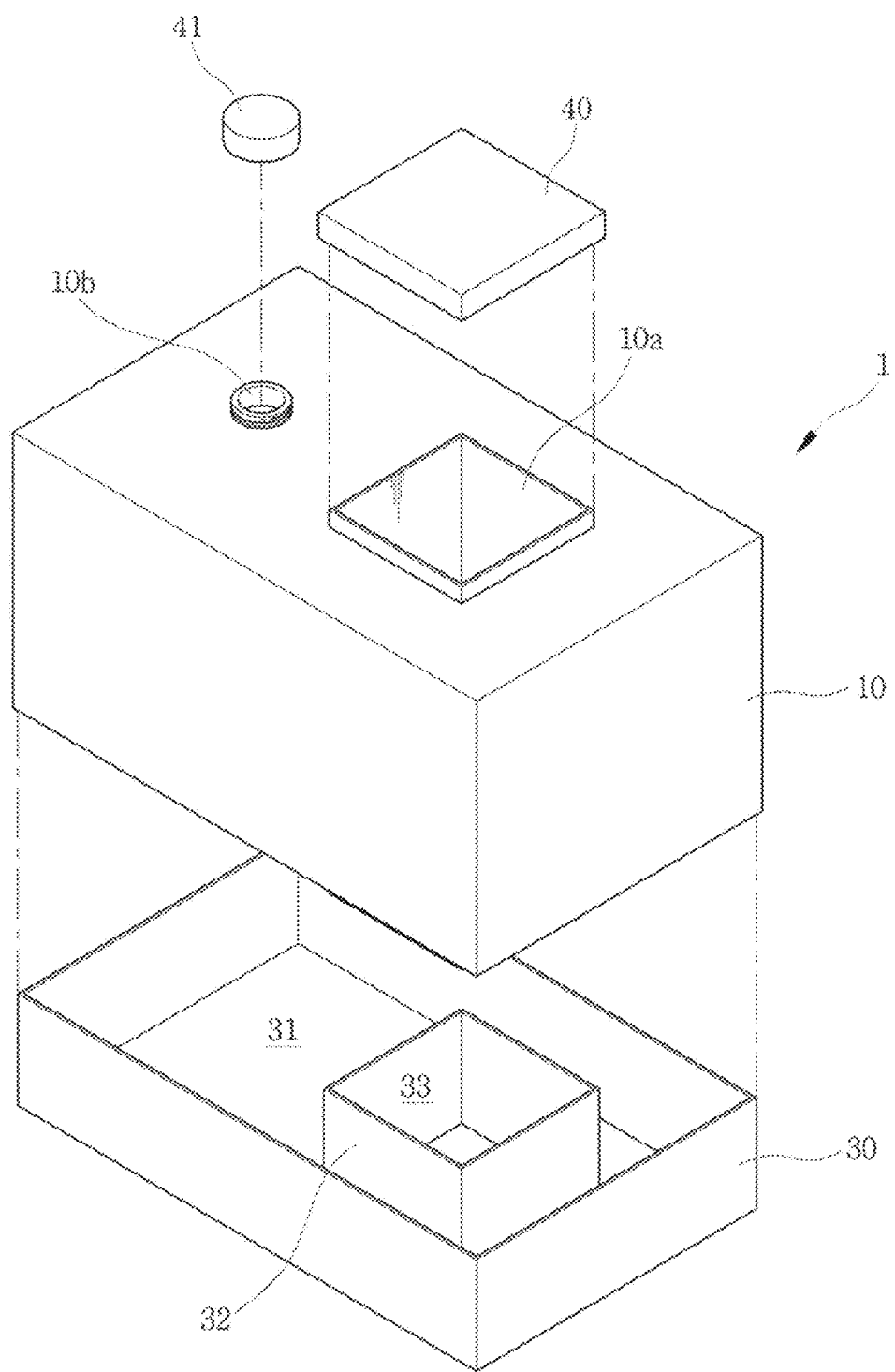
FIG. 4 shows an exploded perspective view of an automated 3D culture system according to an embodiment of the present disclosure.

FIG. 4 shows an exploded perspective view of the automated 3D culture system 1 according to an embodiment of the present disclosure, in which the first body 10 and the second body 30 are separated and configured to be disassembled and assembled, and the first lid 40 and the second lid 41 are provided above the first body 10.

Referring to FIGS. 1 to 4, in the automated 3D culture system 1 according to an embodiment of the present disclosure, the first body 10 includes the cell culture space 11 independently provided therein in which a scaffold 2 for culturing cells is placed and cells are cultured, and the medium storage space 13 independently provided therein in which a medium or media is injected and stored.

That is, the first body 10 includes the cell culture space 11 and the medium storage space 13 surrounding the same, wherein the cell culture space 11 is separated from the medium storage space 13. This configuration may be easily made by partitioning the cell culture space 11 and the medium storage space 13 through the first partition wall 12.

Here, the cell culture space 11 may have an upper portion having an opening 10a through which the scaffold 2, prepared in the form of a gel by using an agarose composition or a polymer material, is inserted from the outside. The scaffold 2 introduced through the opening 10a is placed on a bottom portion 11a of the cell culture space 11.

In addition, an inlet part 10b is formed above the medium storage space 13 to allow the medium to be provided thereinto. In this case, the inlet part 10b may not be formed above the medium storage space 13. In an embodiment, the inlet part 10b may be formed on side surfaces of the medium storage space 13 as long as the medium is easily provided.

The lower end 13a of the medium storage space 13 may be formed to have a horizontal cross-section which is formed in a diagonal direction or constitutes a V-shaped valley with reference to a drain hole 14 so that all the medium provided to the medium storage space 13 is drained to the cell culture space 11.

The first partition wall 12 is a kind of partition for separating the cell culture space 11 from the medium storage space 13, and extends upward from the bottom portion 11a on which the scaffold 2 is placed, and has a drain hole 14 on a side surface thereof to make the cell culture space 11 to communicate with the medium storage space 13 so that the medium is provided on the scaffold 2 on which cells is fed.

The first body 10, in which the cell culture space 11 and the medium storage space 13 separated from each other through the first partition wall 12 are provided therein, may have a polygonal or circular horizontal cross-section, and the first partition wall 12 may be located in the central portion of the first body 10 and may have a polygonal or circular horizontal cross-section.

In an embodiment of the present disclosure, the first partition wall 12 having a rectangular horizontal cross-section is located in the central portion of the first body 10 having a rectangular horizontal cross-section, and the drain hole 14 is formed, while being in contact with the bottom portion 11a of the cell culture space 11, in a lower portion of the first partition wall 12.

Here, the first body 10 may be formed of a transparent material that can be implemented by using, for example, transparent plastic or tempered glass, and through the first body 10, the culture process of the cells may be easily observed from the outside. In an embodiment, only a portion of the first body 10 may be formed of a transparent material to observe the cell culture process.

Meanwhile, the automated 3D culture system 1 according to an embodiment of the present disclosure includes the second body 30 located under the first body 10. The second body 30 includes the communication pipe 20 that is provided on the first partition wall 12 and drains the medium of the cell culture space 11 to the outside by a siphon action, the medium recovery space 31 for recovering and externally draining the medium drained through the communication pipe 20, and the cell observation space 33 for observing cells from the outside, wherein the medium recovery space 31 and the cell observation space 33 are independently provided inside the second body 30.

That is, like the first body 10, the second body 30 includes the medium recovery space 31 and the cell observation space 33 which are separated from each other inside. This configuration may be easily implemented by using the second partition wall 32 partitioning the cell observation space 33 and the medium recovery space 31 surrounding the same.

The second partition wall 32 is formed to extend downward from the bottom portion 11a of the cell culture space 11, so that it is easy to observe the cells through the cell observation space 33. In other words, the cell observation space 33 is opened to the outside through the second partition wall 32, so that compatibility with external devices for photographing the growth of specific parts of the cells or motion patterns thereof may be obtained, and accordingly, the cells may be continuously observed.

The second body 30, in which the cell observation space 33 and the medium recovery space 31 surrounding the same are independently provided through the second partition wall 32, may have a polygonal or circular horizontal cross-section, and the second partition wall 32 having the polygonal or circular horizontal cross-section may be located at the central portion of each of the first body 10 and the second body 30.

In an embodiment of the present disclosure, the second partition wall 32 having a rectangular horizontal cross-section is located in the central portion of the second body 30 having a square horizontal cross-section.

Here, the second body 30, like the first body 10, may be formed of a transparent material that can be implemented with, for example, transparent plastic or tempered glass. Accordingly, the cell culture process may be easily observed from the outside. In an embodiment, only a portion of the second body 30 may be formed of a transparent material to observe the culture process of cells, and the second body 30 may be configured integrally with the first body 10 or may be configured separately to be disassembled and assembled.

In addition, in the case of the automated 3D culture system 1, in which the first body 10 and the second body 30 are integrally formed, the drain port 30a for external drainage of the medium may be provided at the lower portion of the second body 30.

The communication pipe 20 may be provided on the first partition wall 12 to drain the medium of the cell culture space 11 to the medium recovery space 31 by a siphon action. Here, the communication pipe 20 may be located opposite to the drain hole 14 or may be located in such a direction that the communication pipe 20 crosses the drain hole 14, and may be formed integrally with the first partition wall 12.

That is, the communication pipe 20 may be provided on the first partition wall 12 located opposite to the drain hole 14 such that one end of the communication pipe 20 is bent and disposed above the bottom portion 11a of the cell culture space 11, and the other end thereof is placed at a position lower than the end and in the upper portion of the medium recovery space 31. Accordingly, due to a siphon action that acts based on the principle of a siphon using the liquid being pushed up into a tube due to atmospheric pressure acting on a liquid surface on the higher side, the medium of the cell culture space 11 is drained into the medium recovery space 31.

Therefore, according to an embodiment of the present disclosure, when the medium supplied to the cell culture space 11 is filled up to the maximum level of the communication pipe 20, the medium is drained to the medium recovery space 31 through the communication pipe 20 by a siphon action. The medium recovered in the medium recovery space 31 may be finally drained to the outside of the automated 3D culture system 1 by separating the second body 30 from the first body 10 or through the drain port 30a.

Hereinafter, the cell culture process using the automated 3D culture system according to an embodiment of the present disclosure will be described in detail as follows.

FIG. 5 shows a cross-sectional view of the automated 3D culture system 1 according to an embodiment of the present disclosure to describe a cell culture process. The scaffold 2 and cells are introduced into the cell culture space 11 separated from the medium storage space 13 by the first partition wall 12, and after the medium, which has been provided into the medium storage space 13, is provided to the cell culture space 11 through the drain hole 14, the medium is recovered to the medium recovery space 31 through the communication pipe 20 due to the siphon action.

That is, as shown in FIG. 5, in the cell culture process using the automated 3D culture system 1 according to an embodiment of the present disclosure, a medium is provided to the medium storage space 13 through the inlet part 10b, and then the second lid 41 is coupled to the inlet part 10b to seal the medium storage space 13. Then, the scaffold 2 and cells are placed in the cell culture space 11 through the opening 10a, and an appropriate amount of medium is provided, and then, the first lid 40 is coupled to the opening 10a to seal the cell culture space 11.

Accordingly, the automated 3D culture system 1 according to an embodiment of the present disclosure further includes the first lid 40 for opening and closing the cell culture space 11 and the second lid 41 for opening and closing the medium storage space 13. In addition, each of the first lid 40 and the second lid 41 may be provided with a sealing pad 42 thereinside to seal the cell culture space 11 and the medium storage space 13.

Herein, the cell culture process using the automated 3D culture system 1 according to an embodiment of the present disclosure, that is, the process of providing the medium into the medium storage space 13 and the process of providing the scaffold 2 and the cells into the cell culture space 11 may be performed in a clean bench.

Meanwhile, 3 to 4 days after providing the medium to the medium storage space 13, the inlet part 10b is partially opened through the second lid 41 to allow the medium to flow out through the drain hole 14. Here, when the medium is filled to the maximum level of the communication pipe 20, the second lid 41 is completely closed to seal the medium storage space 13.

When the medium is filled to the maximum level of the communication pipe 20, the medium in the cell culture space 11 is drained into the medium recovery space 31 by a siphon action. In detail, when the medium is filled by the maximum level of communication pipe 20, the pressure of the medium becomes the same as the direction of gravity as the medium reaches the maximum level (height) of the communication pipe 20, and accordingly, the medium is drained into the medium recovery space 31.

The medium is drained through the communication pipe 20, and, when the level of the medium in the cell culture space 11 is lower than the lowermost portion of an end of the communication pipe 20, the draining of the medium is stopped.

Afterwards, when the inlet part 10b is partially opened again using the second lid 41 to fill the cell culture space 11 with the medium, the second lid 41 is closed to seal the medium storage space 13 again, and once the medium fills as high as the maximum level of the communication pipe 20, due to the siphon action, the medium is drained from the cell culture space 11 to the medium recovery space 31.

Here, the lowermost portion of the end of the communication pipe 20 is disposed above the bottom portion 11a, and may be positioned higher than the drain hole 14 of the first partition wall 12. As described above, when the level of the medium in the cell culture space 11 is lower than the lowermost portion of the end of the communication pipe 20, the siphon action stops.

At this time, when the drain hole 14 is formed at a position higher than the lowermost portion of the end of the communication pipe 20, the medium may be continuously drained while the level of the medium in the cell culture space 11 is not lowered than the lowermost portion of the end of communication pipe 20. Therefore, to repeat the process of draining, stopping, and draining of the medium, the lowermost portion of the end of the communication pipe 20 may be positioned higher than the drain hole 14 of the first partition wall 12.

Through these processes, the automated 3D culture system 1 according to an embodiment of the present disclosure may circulate the medium in a one-way low manner to supply the same to cells for a long period of time, thereby enabling long-term cultivation of cells.

In addition, in the case where the medium is recovered and filled in the medium recovery space 31, the medium may be drained externally and then provided to the medium storage space 13 to supply the same to the cells, and this process can be performed repeatedly. Accordingly, the cell culture may be performed for, for example, 30 to 60 days.

Therefore, according to an embodiment of the present disclosure, it is effective in terms of being able to easily culture cells into artificial organs such as the skin, the liver, or the heart that require long-term culture of cells.

Hereinbefore, the present disclosure has been described in detail using embodiments. However, the embodiments are provided herein only to describe the present disclosure in detail, and the automated 3D culture system according to the present disclosure is not limited thereto. The terms such as "includes", "forms", or "comprises" described above mean that a corresponding component may be included unless stated otherwise, and, accordingly, other components may be further included, not excluded. All terms, including technical or scientific terms, unless defined otherwise, have the same meaning as commonly understood by one of ordinary skill in the technical field to which the present disclosure belongs.

In addition, the above description is merely illustrative of the technical concept of the present disclosure, and one of ordinary skill in the technical field to which the present disclosure belongs, may make various modifications and transformations without departing the same from the essential characteristics of the present disclosure. Accordingly, the embodiments disclosed in the present disclosure are not intended to limit the technical concept of the present disclosure, but to describe the same, and the scope of the technical concept of the present disclosure is not limited by this embodiments. The scope of protection of the present disclosure should be interpreted by the scope of the claims below, and all technical concepts within the equivalent scope thereof should be construed as being included in the scope of the present disclosure.

The invention claimed is:

1. An automated three-dimensional (3D) culture system comprising:
   a first body comprising:
      a cell culture space in which a scaffold, on which cells are configured to be cultured, is provided and the cells are configured to be cultured thereon, and
      a medium storage space which is partitioned from the cell culture space by a first partition wall, in which a medium is provided and stored, and which surrounds the cell culture space,
      wherein the first partition wall has a drain hole to communicate the medium storage space with the cell culture space so that the medium provided in the medium storage space is drained to the cell culture space through the drain hole;
   a communication pipe provided at the first partition wall to drain the medium of the cell culture space drained through the drain hole to an outside of the cell culture space by a siphon action; and
   a second body comprising:

a medium recovery space located under the first body and configured to recover and externally drain the medium drained through the communication pipe, and a cell observation space partitioned from the medium recovery space by a second partition wall to observe cells from the outside.

2. The automated 3D culture system of claim 1, wherein the first body and the second body are integrally formed, and wherein the system further comprises a drain port configured to drain the medium and formed at a lower portion of the second body integrally formed with the first body.

3. The automated 3D culture system of claim 2, wherein each of the first body and the second body has a polygonal or circular horizontal cross-section, and wherein the first partition wall and the second partition wall are located at central portions of the first body and the second body, respectively, each of the first partition wall and the second partition wall having a polygonal or circular horizontal cross-section.

4. The automated 3D culture system of claim 1, wherein the medium storage space comprises a lower end having a horizontal cross-section which is formed in a diagonal direction or constitutes a V-shaped valley with reference to a drain hole.

5. The automated 3D culture system of claim 1, wherein each of the first body and the second body has a polygonal or circular horizontal cross-section, and wherein the first partition wall and the second partition wall are located at central portions of the first body and the second body, respectively, each of the first partition wall and the second partition wall having a polygonal or circular horizontal cross-section.

6. The automated 3D culture system of claim 1, further comprising a first lid configured to open and close the cell culture space and a second lid configured to open and close the medium storage space.

7. The automated 3D culture system of claim 6, wherein each of the first lid and the second lid comprises a sealing pad configured to seal the cell culture space or the medium storage space.

8. The automated 3D culture system of claim 1, wherein the communication pipe is configured to drain the medium of the cell culture space by a siphon action, in response to the medium of the cell culture space being filled as high as a maximum level of the communication pipe.

9. The automated 3D culture system of claim 1, wherein the first body and the second body each comprise a transparent material.

10. The automated 3D culture system of claim 1, wherein the communication pipe comprises a first end disposed above a bottom portion of the cell culture space and a second end disposed lower than the bottom portion of the cell culture space, and wherein a lowermost portion of the first end of the communication pipe is formed at a position higher than the drain hole of the first partition wall.

11. The automated 3D culture system of claim 1, wherein the first body and the second body are separated so as to be disassembled and assembled.

* * * * *